United States Patent

Johnson, Jr. et al.

[11] Patent Number: 5,438,979
[45] Date of Patent: Aug. 8, 1995

[54] NASAL CANNULA SUPPORT

[75] Inventors: Arthur L. Johnson, Jr., Loves Park; Tracy K. Stenger, Rockford, both of Ill.

[73] Assignee: Johnson Enterprises, Inc., Rockford, Ill.

[21] Appl. No.: 261,392

[22] Filed: Jun. 17, 1994

[51] Int. Cl.⁶ ............................................. A61M 31/00
[52] U.S. Cl. ................. 128/207.18; 128/912; 128/DIG. 26; 604/94
[58] Field of Search .......... 128/200.24, 204.18, 128/207.18, 912, DIG. 26; 604/94

[56] References Cited

U.S. PATENT DOCUMENTS

| | | | |
|---|---|---|---|
| 2,168,705 | 8/1939 | Francisco et al. | 128/207.18 |
| 2,931,358 | 4/1960 | Sheridan | 128/207.18 |
| 3,209,755 | 10/1965 | McCarthy et al. | 128/DIG. 26 |
| 3,400,714 | 9/1968 | Sheridan | 604/94 |
| 4,106,505 | 8/1978 | Salter et al. | 128/206 |
| 4,156,426 | 5/1979 | Gold | 128/207.18 |
| 4,422,456 | 12/1983 | Tiep | 128/207.18 |
| 4,465,067 | 8/1984 | Koch et al. | 128/207.18 |
| 4,480,639 | 11/1984 | Peterson et al. | 128/207.18 |
| 4,559,941 | 12/1985 | Timmons et al. | 128/207.18 |
| 4,915,104 | 4/1990 | Marcy | 128/207.18 |
| 4,915,105 | 4/1990 | Lee | 128/207.18 |
| 5,025,805 | 6/1991 | Nutter | 128/207.18 |

*Primary Examiner*—Edgar S. Burr
*Assistant Examiner*—William J. Deane, Jr.
*Attorney, Agent, or Firm*—Leydig, Voit & Mayer, Ltd.

[57] ABSTRACT

A nasal cannula is supported on the crossbar of a generally U-shaped frame having bows adapted to extend rearwardly along the sides of a patient's head and adapted to rest on the patient's ears. Clips on the crossbar and the bows support flexible tubes for supplying oxygen to the cannula. A strap is connected to the bows and contracts around the rear and sides of the patient's head to help hold the frame in place.

1 Claim, 2 Drawing Sheets

NASAL CANNULA SUPPORT

BACKGROUND OF THE INVENTION

This invention relates generally to a support for a nasal cannula assembly designed for contact with the nasalabidial area of a patient's nose. More particularly, the invention relates to a support for a cannula assembly of the same general type as disclosed in Salter et al U.S. Pat. No. 4,106,505.

The assembly of the Salter et al patent includes a nasal cannula in the form of a hollow tubular member having end portions connected to flexible tubes which communicate with a pressurized source of oxygen or other gas. Hollow tubular extensions project from and communicate with the tubular member and fit into the patient's nostrils to supply the patient with oxygen from the tubes.

In the assembly of the Salter et al patent, the cannula contacts the nasalabidial area between the patient's upper lip and nostrils while the flexible tubes extend upwardly and rearwardly from the cannula and lie against the patient's upper cheeks in proximity to the outer corners of the eyes. The tubes then drape over the patient's ears inboard of the auricles thereof and then extend forwardly around the patient's neck for connection to the oxygen source. A sleeve on the tubes is slid upwardly to hold the tubes loosely under the chin.

Because the cannula is held in place on the patient's head by the tubes, the patient often experiences severe discomfort. The pressure exerted by the tubes against the upper cheeks tends to force the patient's eyes closed, thus interfering with clear vision and causing watering of the eyes. In addition, the tubes rub against the cheeks and the tops of the ears and tend to wear those areas raw. If the patient wears eyeglasses, even more discomfort is present since the bows of the glasses press the relatively small diameter tubes downwardly against the ears. Moreover, the bows tend to slip on the tubes thereby making it difficult to keep the glasses in a square position.

SUMMARY OF THE INVENTION

The general aim of the present invention is to provide a new and improved nasal cannula support which, when compared to prior arrangements, is far more comfortable to wear and is easier to install and remove.

A more detailed object of the invention is to achieve the foregoing by supporting the cannula and the tubes on a generally U-shaped frame which fits comfortably on the patient's head much in the same manner as eyeglasses and which eliminates pressure on the cheeks while reducing pressure on the ears.

The invention also resides in the provision of relatively inexpensive means for attaching the cannula and the tubes to the frame and in the unique provision of a head strap for helping hold the frame on the patient's head.

These and other objects and advantages of the invention will become more apparent from the following detailed description when taken in conjunction with the accompanying drawings.

Figure 1:
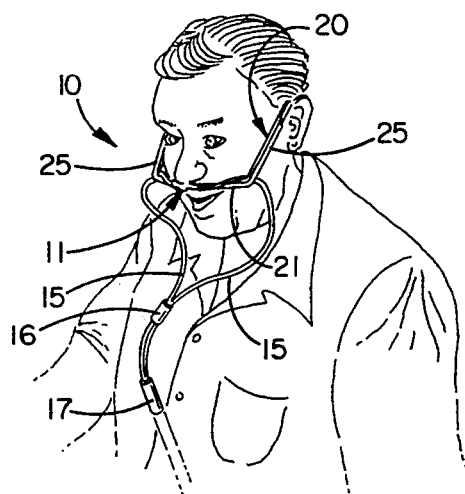
FIG. 1 is a front perspective view of a patient wearing a new and improved cannula support incorporating the unique features of the present invention.
Figure 2:
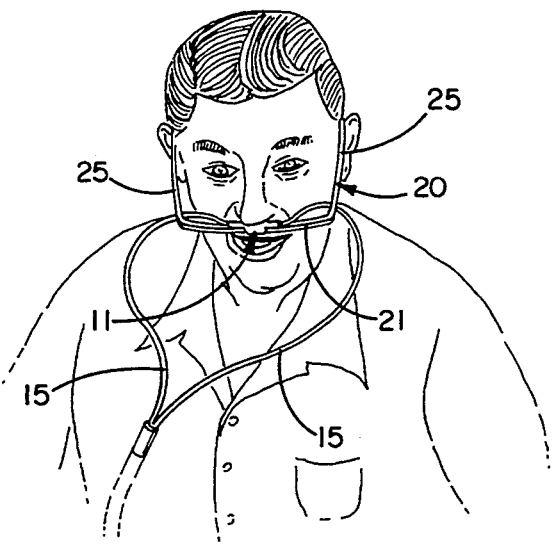
FIGS. 2 and 3 are generally front and side views, respectively, of the patient and the support.
Figure 3:
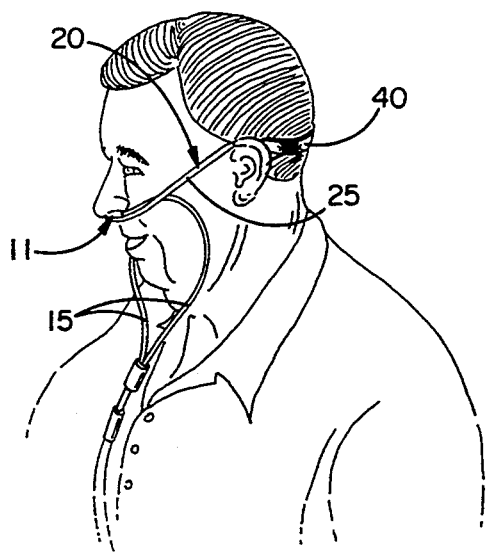
Figure 4:
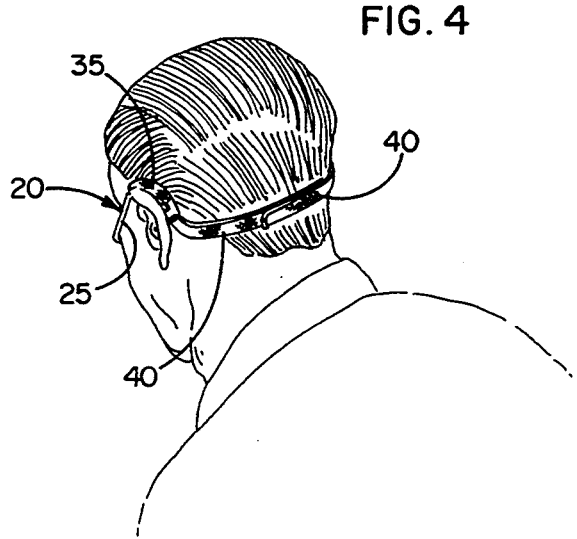
FIG. 4 is a rear perspective view of the patient and the support.

While the invention is susceptible of various modifications and alternative constructions, a certain illustrated embodiment hereof has been shown in the drawings and will be described below in detail. It should be understood, however, that there is no intention to limit the invention to the specific form disclosed, but on the contrary, the intention is to cover all modifications, alternative constructions and equivalents falling within the spirit and scope of the invention.

DETAILED DESCRIPTION OF THE PREFERRED EMBODIMENT

For purposes of illustration, the invention has been shown in the drawings as embodied in a support 10 for a nasal cannula 11 used to supply oxygen or other gas from a pressurized source (not shown) to the nostrils of a patient. The cannula itself is of conventional construction and comprises a soft tubular member 12 (FIGS. 5 and 6) of sufficient length to span the width between a patient's nostrils and having a pair of laterally spaced and hollow extensions 13 adapted to be inserted into the nostrils. The extensions are molded integrally with the tubular member, project generally rearwardly therefrom and terminate in gas directing discharge orifices which communicate with the tubular member.

Opposite ends of the tubular member 12 are open and receive flexible tubes 15 which supply oxygen from the pressurized source to the patient's nostrils via the tubular member and the extensions 13. The distal end portions of the tubes are encircled by a slidable sleeve 16 and carry a fitting 17 which is adapted to be coupled to the oxygen source.

In use, the tubular member 12 of the cannula 11 lies against the patient's nasalabidial area (i.e., the area between the upper lip and the nostrils) while the extensions 13 project into the nostrils and supply oxygen thereto. Some patients require oxygen on substantially a constant basis and thus it is important that the patient be able to comfortably wear the cannula.

In accordance with the present invention, provision is made of a relatively simple and inexpensive cannula support 10 which enables the cannula 11 to fit comfortably on the patient without exerting pressure on the patient's upper cheeks while reducing pressure on the ears and reducing skin irritation resulting from prior cannula assemblies. The support 10 of the present invention is relatively easy to put on and take off and makes it easier for the patient to wear eyeglasses while using the cannula.

More specifically, the cannula support 10 includes a generally U-shaped frame 20 which preferably is of one-piece construction and is molded from a self-supporting but resiliently yieldable plastic such as polypropylene. The frame includes a laterally extending crossbar 21 of sufficient length to extend beyond the sides of the patient's head. The crossbar preferably is of convex curvature on its upper and forward sides and is of concave curvature on its lower and rear sides. Herein, the crossbar is of rectangular cross-section.

Bows 25 are joined to and extend rearwardly from the ends of the crossbar 21. In the present instance, the bows are molded integrally with the crossbar and are capable of flexing outwardly relative to the crossbar by virtue of the resiliency of the plastic so as to enable the support to fit heads of various widths. The bows could, however, be molded as separate pieces and joined to the crossbar by vertically extending pivot pins.

The rear end portions 26 (FIG. 6) of the bows 25 gradually curve downwardly upon progressing rearwardly. The rear end portions of the bows preferably are shaped so that they may rest comfortably on the patient's ears inboard of the auricles thereof without significantly dropping behind or significantly hooking around the ears.

Figure 5:
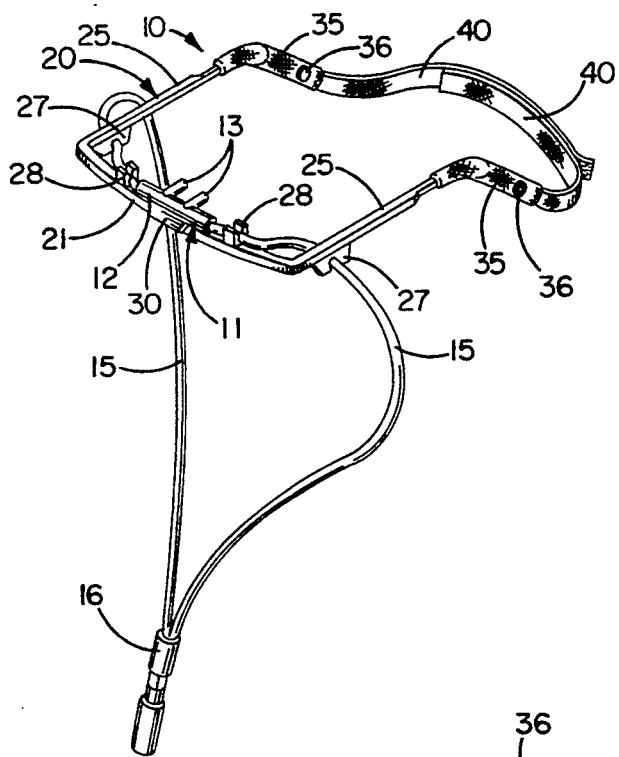
FIG. 5 is a perspective view of the support and the cannula assembly.
Figure 7:
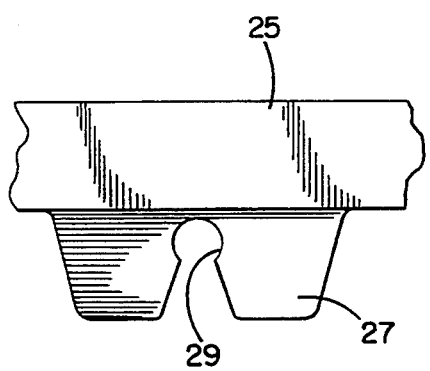
FIG. 7 is an enlarged side elevational view of a portion of the support.
Figure 6:
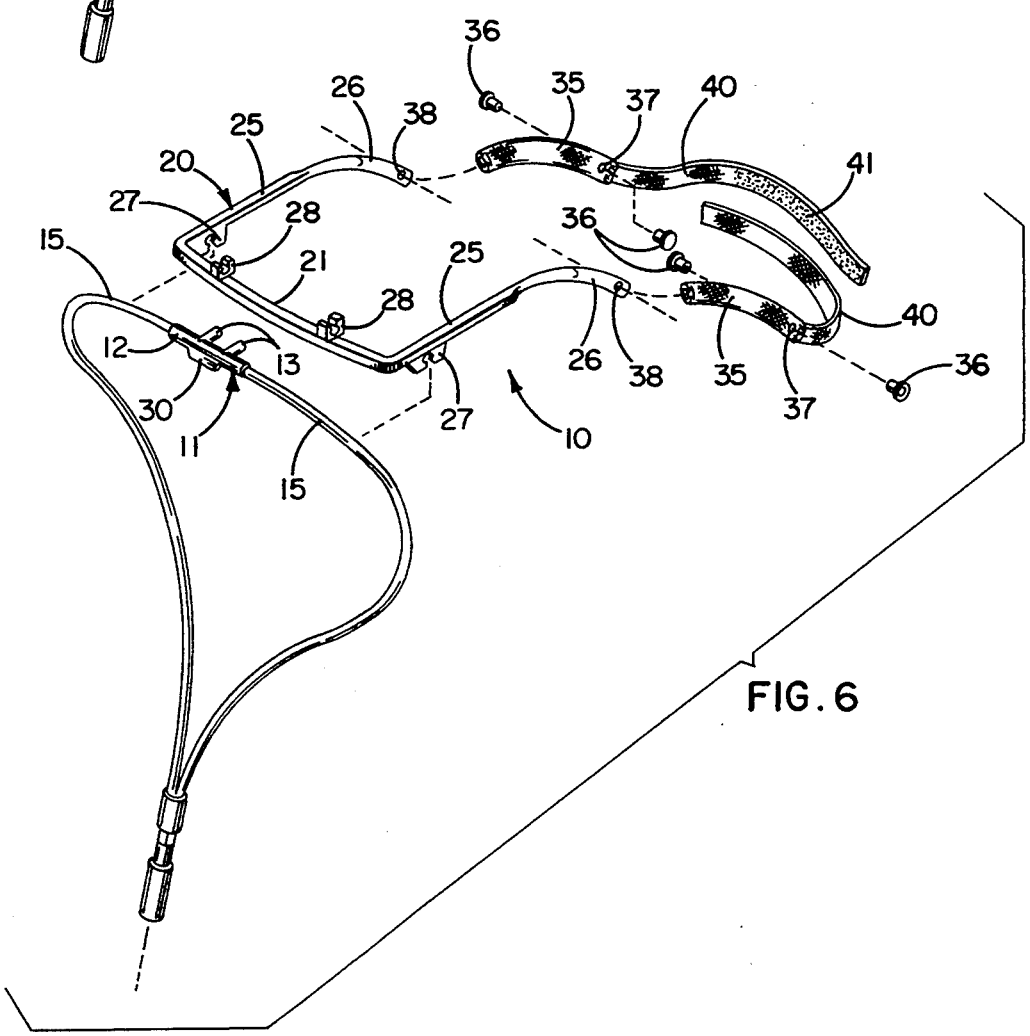
FIG. 6 is an exploded perspective view of the components shown in FIG. 5.

As shown most clearly in FIG. 5, the cannula 11 is adapted to rest on the upper side of the crossbar 21 midway between the ends thereof. Clips 27 and 28 are provided for releasably supporting the cannula on the crossbar. While the clips may be formed separately of and attached to the frame 20, they preferably are molded integrally with the frame. The clips 27 depend from the bows 25 adjacent the junction between the bows and the crossbar 21. Each clip 27 is formed with a downwardly opening notch 29 (FIG. 7) which is appropriately shaped to receive and releasably grip one of the tubes 15. The clips 28 project upwardly from the crossbar 21 in laterally spaced relation with the cannula 11 and are formed with upwardly opening notches similar to the notches 29.

With the foregoing arrangement, the tubes 15 may be snapped into the clips 27 and 28 and positioned as shown in FIG. 5 so as to releasably secure the tubes and the cannula to the frame 20 with the cannula centered laterally on the crossbar 21. Some cannulas include a flap 30 (FIG. 5) depending from the forward side of the tubular member 12 and, in such a case, the flap engages the forward side of the crossbar to help retain the cannula on the crossbar.

In use, the frame 20 is positioned on the patient's head with the crossbar 21 extending laterally across the nasalabidial area, with the bows 25 straddling the sides of the head and with the curved end portions 26 of the bows resting on the tops of the ears inboard of the auricles. When the frame is so positioned, the cannula 11 is held in contact with or in close proximity to the nasalabidial area with the extensions 13 projecting into the nostrils and with the tubes 15 draping downwardly from the clips 27 and 28 and in front of the patient for connection to the oxygen source. A significant advantage of the support 10 is that the tubes do not extend upwardly past and press against the patient's upper cheeks adjacent the eyes. The absence of such pressure eliminates watering of the eyes and eliminates the tendency of the cheeks to be pushed upwardly and cause partial closing of the eyes. As a result, the support 10 enables the patient to wear the cannula 11 without obstruction of vision or discomfort in the eye area. Moreover, the absence of tubes in the cheek areas eliminates skin irritation otherwise resulting from tubes rubbing against those areas.

The support 10 preferably includes means for cushioning the rear end portions 26 of the bows 25 against the tops of the ears and also preferably includes strap means for helping secure the frame 20 to the patient's head. Herein, the cushioning means include sleeves 35 (FIGS. 5 and 6) of soft fabric or other soft material telescoped over the curved end portions 26 of the bows and extending a short distance forwardly along the straight portions of the bows. Suitable fasteners 36 extend through holes 37 (FIG. 6) in the rear end portions of the sleeves 35 and holes 38 near the extreme rear ends of the curved portions 26 of the bows to secure the sleeves to the bows. The sleeves act as cushions between the curved bow portions 26 and the tops of the ears to reduce pressure, rubbing and skin irritation in those areas. The friction of the fabric sleeves against the skin also reduces the tendency of the curved bow portions to slip on the ears and thus helps hold the frame squarely on the patient's face. In addition, patients who wear eyeglasses experience less discomfort by virtue of the fact that the relatively large diameter and soft fabric sleeves cushion the overlying bows of the glasses and reduce slippage thereof.

Herein, the strap means comprise two elastic straps 40 (FIGS. 5 and 6) whose forward ends are sewn to the rear ends of the sleeves 35. The straps carry means 41 such as Velcro to enable the effective length of the overall strap to be easily adjusted for different patients. When the frame 20 is placed on the head, the straps 40 are slipped downwardly from the top of the head to a position behind the head and, after being adjusted in effective length, gently contract around the head to help hold the frame in place.

From the foregoing, it will be apparent that the present invention brings to the art a new and improved cannula support 10 which greatly reduces the discomfort experienced by a patient required to wear the cannula 11. In addition to being comfortable to wear, the support does not interfere with vision, enables the patient to wear and easily put on and remove eyeglasses, is itself easy to install and remove, and is relatively simple and inexpensive by virtue of the one-piece frame 20.

We claim:

1. In combination, a support and a nasal cannula assembly designed to be located proximate the nasalabidial area of a patient, said assembly comprising a hollow tubular member having opposite ends with gas supply openings, said tubular member being of sufficient length to span the width of an average patient's nostrils, said tubular member having a pair of laterally spaced and hollow extensions extending therefrom and communicating therewith and terminating in gas directing orifices, and elongated flexible tubes connected to and extending from the gas supply openings of said tubular member and adapted for connection to a pressurized source of gas, said support being generally U-shaped and having a non-gas carrying crossbar extending laterally across the patient's face between the patient's nostrils and upper lip and extending laterally beyond the sides of the patient's head, a pair of non-gas carrying bows molded integrally with and extending rearwardly from said crossbar adjacent the sides of the patient's head and having means for resting on the patient's ears inboard of the auricles thereof, said resting means being molded integrally with said bows, and means for supporting said tubular member on said crossbar in a position to locate said tubular member between the patient's nostrils and under lip and to enable said extensions to fit into the patient's nostrils with said tubes draping downwardly in front of the patient without looping around the patient's head, said support being free of contact with the exterior of the patient's nose above the nostrils thereof.

* * * * *